United States Patent
Han et al.

(10) Patent No.: US 12,174,171 B2
(45) Date of Patent: *Dec. 24, 2024

(54) NANOPORE DEVICE AND METHODS OF ELECTRICAL ARRAY ADDRESSING AND SENSING

(71) Applicant: PALOGEN, INC., Palo Alto, CA (US)

(72) Inventors: Kyung Joon Han, San Jose, CA (US); Jungkee Yoon, Santa Clara, CA (US)

(73) Assignee: PALOGEN, INC., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/240,455

(22) Filed: Aug. 31, 2023

(65) Prior Publication Data

US 2024/0219368 A1    Jul. 4, 2024

Related U.S. Application Data

(63) Continuation of application No. 17/378,889, filed on Jul. 19, 2021, now Pat. No. 11,747,320, which is a continuation of application No. 16/237,570, filed on Dec. 31, 2018, now Pat. No. 11,067,561.

(60) Provisional application No. 62/612,534, filed on Dec. 31, 2017.

(51) Int. Cl.
*G01N 33/487* (2006.01)
*B82Y 15/00* (2011.01)
*B82Y 40/00* (2011.01)
*C12Q 1/6869* (2018.01)
*C12Q 1/6874* (2018.01)
(Continued)

(52) U.S. Cl.
CPC ..... *G01N 33/48721* (2013.01); *C12Q 1/6869* (2013.01); *C12Q 1/6874* (2013.01); *G01N 27/4145* (2013.01); *G01N 27/4146* (2013.01); *G01N 27/44791* (2013.01); *B82Y 15/00* (2013.01); *B82Y 40/00* (2013.01)

(58) Field of Classification Search
None
See application file for complete search history.

(56) References Cited

U.S. PATENT DOCUMENTS 11,067,561 B2 * 7/2021 Han ............... G01N 33/48721
11,747,320 B2 * 9/2023 Han ..................... C12Q 1/6869
204/451

FOREIGN PATENT DOCUMENTS

WO    WO-2015198242 A1 * 12/2015 ........... C12Q 1/6827

* cited by examiner

*Primary Examiner* — J. Christopher Ball
(74) *Attorney, Agent, or Firm* — Vista IP Law Group LLP

(57) ABSTRACT

A method of manufacturing and using a nanofluidic NAND transistor sensor array scheme including a plurality of nanopore channel pillars, a plurality of respective fluidic channels, a plurality of gate electrodes, a top chamber, and a bottom chamber includes placing a sensor substrate in an electrolyte solution comprising biomolecules and DNA. The method also includes placing first and second electrodes in the electrolyte solution (Vpp and Vss of the nanofluidic NAND transistor); forming the nanopore channel pillars; placing the gate electrodes and gate insulators in respective walls of the nanopore channel pillars; applying an electrophoretic bias in the first and second electrodes; applying a bias in the gate electrodes; detecting a change in an electrode current in the electrolyte solution caused by a change in a gate voltage; and detecting a change in a surface charge in nanopore channel electrodes in the respective fluidic channels.

20 Claims, 10 Drawing Sheets

(51) Int. Cl.
*G01N 27/414* (2006.01)
*G01N 27/447* (2006.01)

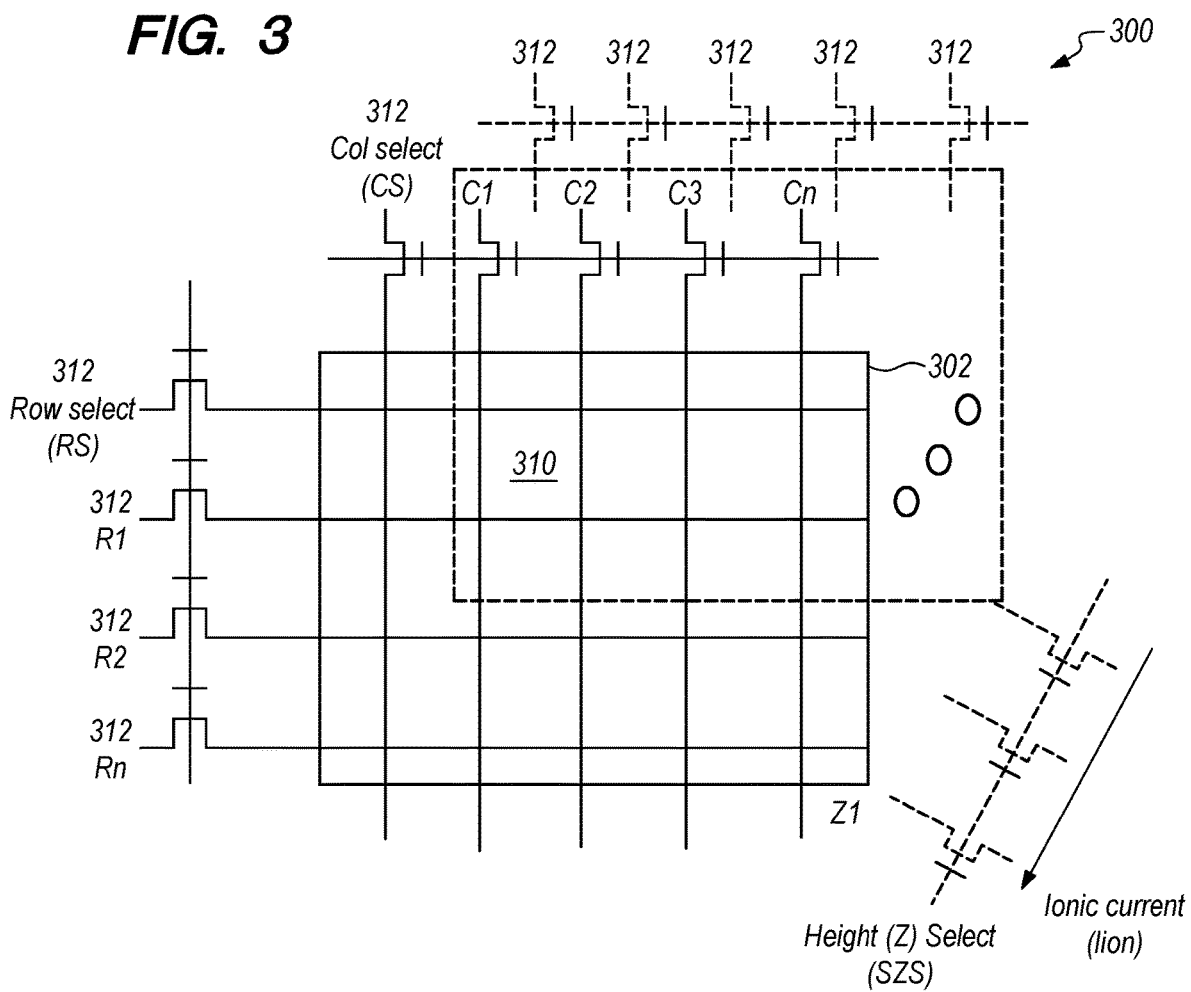

VPP=(0 to +2.5V), VCC=(0 to +1.5V),
IZ (10pA~1uA), other electrodes = GND
I,j (1~N): ($i^{th}$, $j^{th}$) gate electrode

⌐400

| | | VRi | VCi | VZi |
|---|---|---|---|---|
| OPERATION TABLE | | | | |
| ARRAY ADDRESS OPERATION (Inhibitory mode, translocation mode $i^{th}$ electrodes) | Vi (SR/SC) | -VCC | -VCC | VPP / -VPP |
| | Vi (SR/UC) | -VCC | VCC | VPP / -VPP |
| | Vi (UR/SC) | VCC | -VCC | VPP / -VPP |
| | Vi (UR/UC) | VCC | VCC | VPP / -VPP |
| | | VRj | VCj | VZ |
| SENSING OPERATION ($J^{th}$ gate electrodes) | Vj (@Vi) | Vth @ IZ | Vth @ IZ | VPP / -VPP |

*FIG. 4*

NANOPORE DEVICE AND METHODS OF ELECTRICAL ARRAY ADDRESSING AND SENSING

CROSS-REFERENCE TO RELATED APPLICATION

The present application is a continuation of U.S. patent application Ser. No. 17/378,889, filed Jul. 19, 2021 and entitled "NANOPORE DEVICE AND METHODS OF ELECTRICAL ARRAY ADDRESSING AND SENSING," which is a continuation of U.S. patent application Ser. No. 16/237,570, filed Dec. 31, 2018 and entitled "NANOPORE DEVICE AND METHODS OF ELECTRICAL ARRAY ADDRESSING AND SENSING," which claims priority to U.S. Provisional Patent Application Ser. No. 62/612,534, filed on Dec. 31, 2017 and entitled "NANOPORE DEVICE AND METHODS OF ELECTRICAL ARRAY ADDRESSING AND SENSING." This application includes subject matter similar to the subject matter described in U.S. Provisional Patent Application Ser. No. 62/566,313, filed on Sep. 29, 2017 and entitled "MANUFACTURE OF THREE DIMENSIONAL NANOPORE DEVICE"; U.S. Provisional Patent Application Ser. No. 62/593,840, filed on Dec. 1, 2017 and entitled "NANOPORE DEVICE AND METHOD OF MANUFACTURING SAME"; U.S. Provisional Patent Application Ser. No. 62/628,214, filed on Feb. 8, 2018 and entitled "BIOMEMORY FOR NANOPORE DEVICE AND METHODS OF MANUFACTURING SAME"; U.S. Provisional Patent Application Ser. No. 62/711,234, filed on Jul. 27, 2018 and entitled "NANOPORE DEVICE AND METHODS OF DETECTING CHARGED PARTICLES USING SAME"; and U.S. Utility patent application Ser. No. 16/147,362, filed on Sep. 26, 2018 and entitled "NANOPORE DEVICE AND METHOD OF MANUFACTURING SAME." The contents of the above-mentioned applications are fully incorporated herein by reference as though set forth in full.

FIELD OF THE INVENTION

The present invention relates generally to nanopore systems, devices, and processes for characterizing biopolymer molecules, and methods of manufacturing and using such nanopore systems and devices.

BACKGROUND

Nucleic acid (e.g., DNA, RNA, etc.) sequencing is one of the most powerful methods to identify genetic variations at the molecular level. Many signatures of genetic diseases can be diagnosed by information collected through genome-wide single nucleotide polymorphisms ("SNPs") analysis, gene fusion, genomic insertion and deletion, etc. These techniques and other molecular biology techniques require nucleic acid sequencing at some point. Current technologies to sequence nucleic acids at the single molecule level include a nanopore sequencing technology that has advantages over previous sequencing techniques because nanopore sequencing technology has the characteristics of a label-free and amplification-free technique that also has improved read lengths, and improved system throughput. Accordingly, nanopore sequencing technology has been incorporated into high-quality gene sequencing applications.

Early experimental systems for nanopore based DNA sequencing detected electrical behavior of ssDNA passing through an α-hemolysin (αHL) protein nanopore. Since then, nanopore based nucleic acid sequencing technology has been improved. For instance, solid-state nanopore based nucleic acid sequencing replaces biological/protein based nanopores with solid-state (e.g., semiconductor, metallic gates) nanopores, as described below.

A nanopore is a small hole (e.g., with a diameter of about 1 nm to about 100 nm) that can detect the flow of charged particles (e.g., ions, molecules, etc.) through the hole by the change in the ionic current and/or tunneling current. Because each nucleotide of a nucleic acid (e.g., adenine, cytosine, guanine, thymine in DNA, uracil in RNA) affects the electric current density across the nanopore in a specific manner as it physically passes through the nanopore, measuring changes in the current flowing through a nanopore during translocation results in data that can be used to directly sequence a nucleic acid molecule passing through the nanopore. As such, Nanopore technology is based on electrical sensing, which is capable of detecting nucleic acid molecules in concentrations and volumes much smaller than that required for other conventional sequencing methods. Advantages of nanopore based nucleic acid sequencing include long read length, plug and play capability, and scalability. However, current biological nanopore based nucleic acid sequencing techniques can require a fixed nanopore opening (e.g., with a diameter of about 2 nm), have poor sensitivity (i.e., unacceptable amount of false negatives), high cost that renders production worthy manufacturing a challenge, and strong temperature and concentration (e.g., pH) dependency.

With advancements in semiconductor manufacturing technologies, solid-state nanopores have become an inexpensive and superior alternative to biological nanopores partly due to the superior mechanical, chemical and thermal characteristics, and compatibility with semiconductor technology allowing the integration with other sensing circuitry and nanodevices. However, current nanopore DNA sequencing techniques (e.g., involving biological and/or solid-state nanopores) continue to suffer from various limitations, including low sensitivity and high manufacturing cost. FIG. 1 schematically depicts a state-of-art solid-state based 2-dimensional ("2D") nanopore sequencing device 100. While, the device 100 is referred to as "two dimensional," the device 100 has some thickness along the Z axis.

Many of the limitations of nanopore DNA sequencing techniques result from the intrinsic nature of nanopore devices and techniques that must overcome the fast translocation speed and small size (e.g., height of about 0.34 nm and diameter of about 1 nm) of a single nucleotide. Conventional electronic instrumentation (e.g., nanoelectrodes) cannot resolve and sense such fast moving and small nucleotides using conventional nanopore based DNA sequencing techniques. Also high manufacturing cost prevents wider applications of nanopore based DNA sequencing.

In order to address the drawbacks (sensitivity and manufacturing cost) of current state-of-art nanopore technologies, multi-channel nanopore array which allows parallel processing of biomolecule sequencing may be used to achieve label-free, amplification-free, and rapid sequencing. Examples of such multi-channel nanopore arrays are described in U.S. Provisional Patent Application Ser. Nos. 62/566,313 and 62/593,840 and U.S. Utility patent application Ser. No. 16/147,362, the contents of which have been previously incorporated by reference. Since there is no known approach to electrically address such multi-channel nanopore arrays, in order to direct charged particles (e.g., biomolecules) to specific channels in such multi-channel nanopore arrays, some arrays are coupled to microfluidic channels outside the array. Other arrays operate using optical bead techniques by applying labels to charged particles before loading into the array sequencing to direct charged particles to specific channels in such nanopore arrays. Electrically addressing and sensing individual nanopore channels within multi-channel nanopore arrays can facilitate more efficient and effective use of multi-channel nanopore arrays to achieve low cost and high throughput sequencing of charged particles (e.g., biomolecules).

There is a need for nanopore based sequencing systems and devices that address the shortcomings of currently-available sensing configurations, particularly for nanopore array based sequencing systems and devices, which can be electrically addressed and sensed without labels, optical system or other means.

There are many efforts to use nanopore device in arrays to improve manufacturing throughput and lower the cost for nanopore devices (e.g., for sensors). Optical means such as Total Internal Reflection Fluorescence (TIRF) microscopy have been used to detect pore blockade in many nanopores in parallel by monitoring the fluorescence signal from proteins, DNA and many other applications. Nanopore sequencing using ionic current recording in planar bilayers, utilizing enzymes has been developed by Oxford Nanopore Technologies with 512 active channels per chip (MiNIon™) introduced in 2015. Based on typical nanopore sequencing speeds (about 28 ms per nucleotide), in order to sequence a total of $3 \times 10^9$ bases (with 10× coverage) in 15 minutes requires about one million ($10^6$) nanopores. However, current state of art nanopore arrays have less than 1,000 ($10^3$) nanopores due to difficulty in separating readings (sensed signals) from various nanopores in the arrays. There is no known method currently available to address and sense the high density nanopore array devices with sufficient reliability (e.g., accuracy) to meet the biomolecule sequencing requirements.

Nanopore sensing method generally uses resistive pulse sensing (i.e., Coulter counter technique, also known as "ionic blockade current technique") that monitors detectable ionic current modulations created as individual analyte molecules pass through or interact with the nanopore pillar channel and generate a blockade in the nanopore pillar channel. Other I-V measurement techniques detect modulations in the surface charge of the wall of the nanopore pillar channel resulting from interaction of analyte molecules with the nanopore pillar channel wall. Such surface charge modulations can manifest in resistance change in the I-V sensing modality. Other sensing techniques include tunneling, plasmonic, and optical sensing. However, many of these sensing techniques suffer from high bandwidth electrical noise and low throughput associated with high translocation speed, making the electrical implementation of nanopore sensing very challenging.

SUMMARY

Embodiments described herein are directed to nanopore based sequencing systems and methods of sensing using same. In particular, the embodiments are directed to various types (2D or 3D) of nanopore based sequencing systems, methods of using nanopore array devices, and methods of sensing using same.

In one embodiment, a nanopore device for characterizing biopolymer molecules includes a first selecting layer having a first plurality of independently addressable inhibitory electrodes disposed along a first axis of selection. The device also includes a second selecting layer having a second plurality of independently addressable inhibitory electrodes disposed along a second axis of selection orthogonal to the first axis of selection, where the second selecting layer is disposed adjacent the first selecting layer. The device further includes a third electrode layer having a third independently addressable electrode, where the third electrode layer is disposed adjacent the second selecting layer, such that the first selecting layer, the second selecting layer, and the third electrode layer form a stack of layers along a Z axis and define a plurality of nanopore pillars. The first and second pluralities of inhibitory electrodes form an array, such that the first plurality of inhibitory electrodes surround each of the plurality of nanopore pillars along the first axis of selection, and the second plurality of inhibitory electrodes surround each of the plurality of nanopore pillars along the second axis of selection.

In one or more embodiments, the plurality of nanopore pillars is disposed in an array of nanopore pillars along a plane orthogonal to the Z axis. Each of the first plurality of inhibitory electrodes may be independently addressable to select a respective row of nanopore pillars from the array of nanopore pillars. Each of the second plurality of inhibitory electrodes may be independently addressable to select a respective column of nanopore pillars from the array of nanopore pillars. One of the first plurality of inhibitory electrodes and one of the second plurality of inhibitory electrodes may be independently addressable to select a nanopore pillar from the array of nanopore pillars.

In one or more embodiments, the first and second pluralities of inhibitory electrodes are cross-patterned electrodes. Each pair of the first plurality of inhibitory electrodes may be independently addressable to select a respective row of nanopore pillars from the array of nanopore pillars. Each pair of the second plurality of inhibitory electrodes may be independently addressable to select a respective column of nanopore pillars from the array of nanopore pillars. Respective pairs of the first and second pluralities of inhibitory electrodes may be independently addressable to select a nanopore pillar from the array of nanopore pillars.

In one or more embodiments, the first and second pluralities of inhibitory electrodes are configured to select a nanopore pillar from the array of nanopore pillars by applying a first inhibitory bias to all of the first plurality of inhibitory electrodes except a first inhibitory electrode corresponding to a selected row and applying a second inhibitory bias to all of the second plurality of inhibitory electrodes except a second inhibitory electrode corresponding to a selected column. The first and second inhibitory biases may generate respective first and second electric fields sufficient to suppress ionic translocation.

In one or more embodiments, the first and second electrodes are independently addressable to modify a translocation rate through the plurality of nanopore pillars. Sufficiently high positive gate voltage applied to the first and second inhibitory electrodes compared to the anode to cathode (i.e., top to bottom chamber) bias will inhibit the ionic current flow to a level such that enables a column (first electrode plane) and row (second electrode plane) array addressing scheme. The third electrode may also be independently addressable to modify its ionic charge state and thus change the surface charge of the selected (by the first and second electrodes) nanopore channel from the plurality of nanopore pillars and modify a translocation rate therethrough.

The third through $N_{th}$ electrode may be independently addressable through nanoelectrode gate modulation. While applying the positive Vpp on the anode electrode of the electrolyte in the top chamber, applying a counter (positive) gate voltage to the third electrode will decrease the translation rate by decreasing the ionic current flow.

In one or more embodiments, the third through $N_{th}$ electrode is independently addressable to modify a translocation rate through the plurality of nanopore pillars. The third electrode may be independently addressable to modify a surface charge of a wall of a nanopore pillar from the plurality of nanopore pillars to modify a translocation rate therethrough. The third electrode may be independently addressable through nanoelectrode gate modulation. Applying a positive gate voltage to the third electrode may increase the translation rate. Applying a negative gate voltage to the third electrode may decrease the translation rate.

In one or more embodiments, the third through $N_{th}$ electrode is independently addressable to sense a change in an electrical characteristic related to the plurality of nanopore pillars. The third through $N_{th}$ electrode may be independently addressable to detect the electrical characteristic using resistive pulse sensing, current-voltage sensing, Coulter counter technique, ionic blockade current technique, tunneling current technique, plasmonic sensing, or optical sensing.

The third through $N_{th}$ electrode may be independently addressable to apply a voltage pulse in a transverse direction to the plurality of nanopore pillars. The third electrode may be independently addressable to sense a transconductance change resulting from the voltage pulse.

In one or more embodiments, the device also includes a fourth electrode layer having a fourth independently addressable electrode. The fourth electrode layer may be disposed adjacent an opposite side of the third electrode layer from the second selecting layer, such that the first selecting layer, the second selecting layer, the third electrode layer, and the fourth electrode layer form an expanded stack of layers along the Z axis and define the plurality of nanopore pillars. The third electrode may be independently addressable to sense a time of flight measurement based on a time interval between signals sensed at the third and fourth electrode layers.

In one or more embodiments, for the effective ionic molecule modulation, the device can operate in the opposite direction (trans being the drain to cis-being the source) and the bottom electrode layers becoming column and row addressable inhibit layers) such that inhibit layers can be are selected from the bottom layers. The fourth electrode layer on the top may be disposed adjacent an opposite side of the third electrode layer from the second selecting layer, such that the first selecting layer, the second selecting layer, the third electrode layer, and the fourth electrode layer form an expanded stack of layers along the Z axis and define the plurality of nanopore pillars. The third electrode may be independently addressable to sense a time of flight measurement based on a time interval between signals sensed at the third and fourth electrode layers.

In one or more embodiments, all gate electrodes can be a cross-coupled configuration, allowing addressability.

In one or more embodiments, each of the first and second pluralities of inhibitory electrodes and the third and fourth electrodes are all nanoelectrodes. The nanopore device may form part of a solid-state, biological, or hybrid system. The nanopore device may form part of a 3D system. The nanopore device may form part of a 2D system.

In another embodiment, a method of manufacturing and using a nanofluidic NAND transistor sensor array scheme comprising a plurality of nanopore channel pillars, a plurality of respective fluidic channels, a plurality of gate electrodes, a top chamber, and a bottom chamber includes placing a sensor substrate in an electrolyte solution comprising biomolecules and DNA. The method also includes placing first and second electrodes in the electrolyte solution in the top and bottom chambers (Vpp and Vss of the NAND transistor). The method further includes forming the plurality of nanopore channel pillars in the sensor substrate. Moreover, the method includes placing the plurality of gate electrodes in respective walls of the plurality of nanopore channel pillars. In addition, the method includes placing a plurality of gate insulators between the plurality of vertical nanopore channel pillars and the plurality of gate electrodes to separate the plurality of vertical nanopore channel pillars from the plurality of gate electrodes. The method also includes applying an electrophoretic bias in the first and second electrodes in the electrolyte solution in the top and bottom chambers. The method further includes applying a bias in the plurality of gate electrodes in the respective walls of the plurality of nanopore channel pillars. Moreover, the method includes detecting a change in an electrode current in the electrolyte solution caused by a change in a gate voltage. In addition, the method includes detecting a change in a surface charge in a plurality of nanopore channel electrodes in the plurality of respective fluidic channels.

In one or more embodiments, the plurality of nanopore channel pillars forms part of a 3D or 2D system.

In another embodiment, a nanopore device for characterizing biopolymer molecules includes a plurality of arrays disposed along a longitudinal axis. Each array has a first selecting layer having a first plurality of independently addressable electrodes disposed along a first axis of selection; and a second selecting layer having a second plurality of independently addressable electrodes disposed along a second axis of selection orthogonal to the first axis of selection. The first plurality of independently addressable electrodes surrounds each of a plurality of nanopore pillars along the first axis of selection. The second plurality of independently addressable electrodes surrounds each of the plurality of nanopore pillars along the second axis of selection.

In one or more embodiments, a top array of the plurality includes first and second inhibitory electrodes. The other arrays of the plurality may include translocation rate control and sensing electrodes.

In one or more embodiments, a bottom array of the plurality includes first and second inhibitory electrodes. The other arrays of the plurality may include translocation rate control and sensing electrodes.

The aforementioned and other embodiments of the invention are described in the Detailed Description which follows.

BRIEF DESCRIPTION OF THE DRAWINGS

The foregoing and other aspects of embodiments are described in further detail with reference to the accompanying drawings, in which the same elements in different figures are referred to by common reference numerals, wherein:

FIG. 3 schematically illustrates a 3D nanopore device according to one embodiment including some details of its operation.

FIG. 4 is a table summarizing the voltage operation of the nanopore device depicted in FIG. 3.

Figure 1:
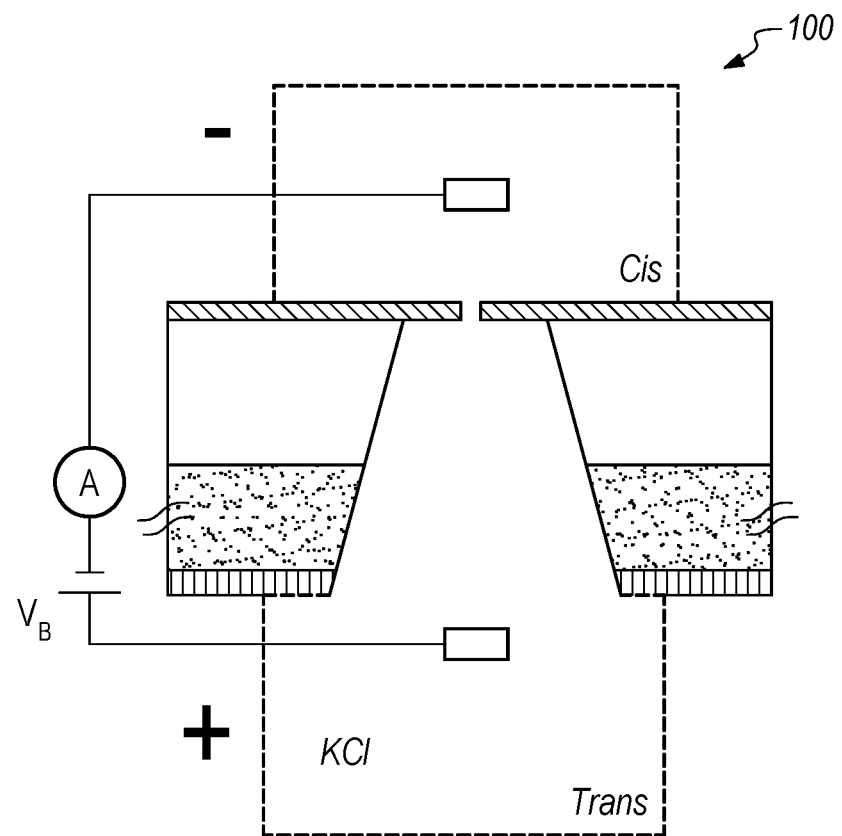
FIG. 1 schematically illustrates a prior art solid-state 2D nanopore device.

In order to better appreciate how to obtain the above-recited and other advantages and objects of various embodiments, a more detailed description of embodiments is provided with reference to the accompanying drawings. It should be noted that the drawings are not drawn to scale and that elements of similar structures or functions are represented by like reference numerals throughout. It will be understood that these drawings depict only certain illustrated embodiments and are not therefore to be considered limiting of scope of embodiments.

DETAILED DESCRIPTION OF ILLUSTRATED EMBODIMENTS

In order to address the above-described drawbacks (sensitivity and manufacturing cost) of current state-of-art nanopore technologies, multi-channel nanopore arrays that allow parallel processing of biomolecule sequencing may be used to achieve label-free, amplification-free, and rapid biomolecule sequencing. Examples of such multi-channel nanopore arrays are described in U.S. Provisional Patent Application Ser. Nos. 62/566,313 and 62/593,840 and U.S. Utility patent application Ser. No. 16/147,362, the contents of which have been previously incorporated by reference. Since there is no known approach to electrically address such multi-channel nanopore arrays, in order to direct charged particles (e.g., biomolecules) to specific channels in such multi-channel nanopore arrays, some arrays are coupled to microfluidic channels outside the array. Other arrays operate using optical bead techniques by applying labels to the charged particles before loading into the array for sequencing to direct charged particles to specific channels in such multi-channel nanopore arrays. Electrically addressing and sensing individual nanopore channels within multi-channel nanopore arrays can facilitate more efficient and effective use of multi-channel nanopore arrays to achieve low cost and high throughput sequencing of charged particles (e.g., biomolecules).

Methods of efficiently and effectively addressing and sensing the multi-channel nanopore arrays using electrical biasing through nanoelectrodes embedded in the nanopore arrays according to various embodiments are described below. Such electrical addressing and sensing techniques can be used in solid-state nanopore arrays, biological arrays and hybrid nanopore arrays. Such electrical addressing and sensing techniques can also be used with various multi-channel nanopore arrays, including the 3D multi-channel nanopore arrays described above and planar multi-channel nanopore arrays.

Exemplary Nanopore Devices

As described above, current state-of-art nanopore devices are limited at least in terms of sensitivity and manufacturing cost. The nanopore device embodiments described herein address, inter alia, these limitations of current nanopore devices.

Figure 2A:
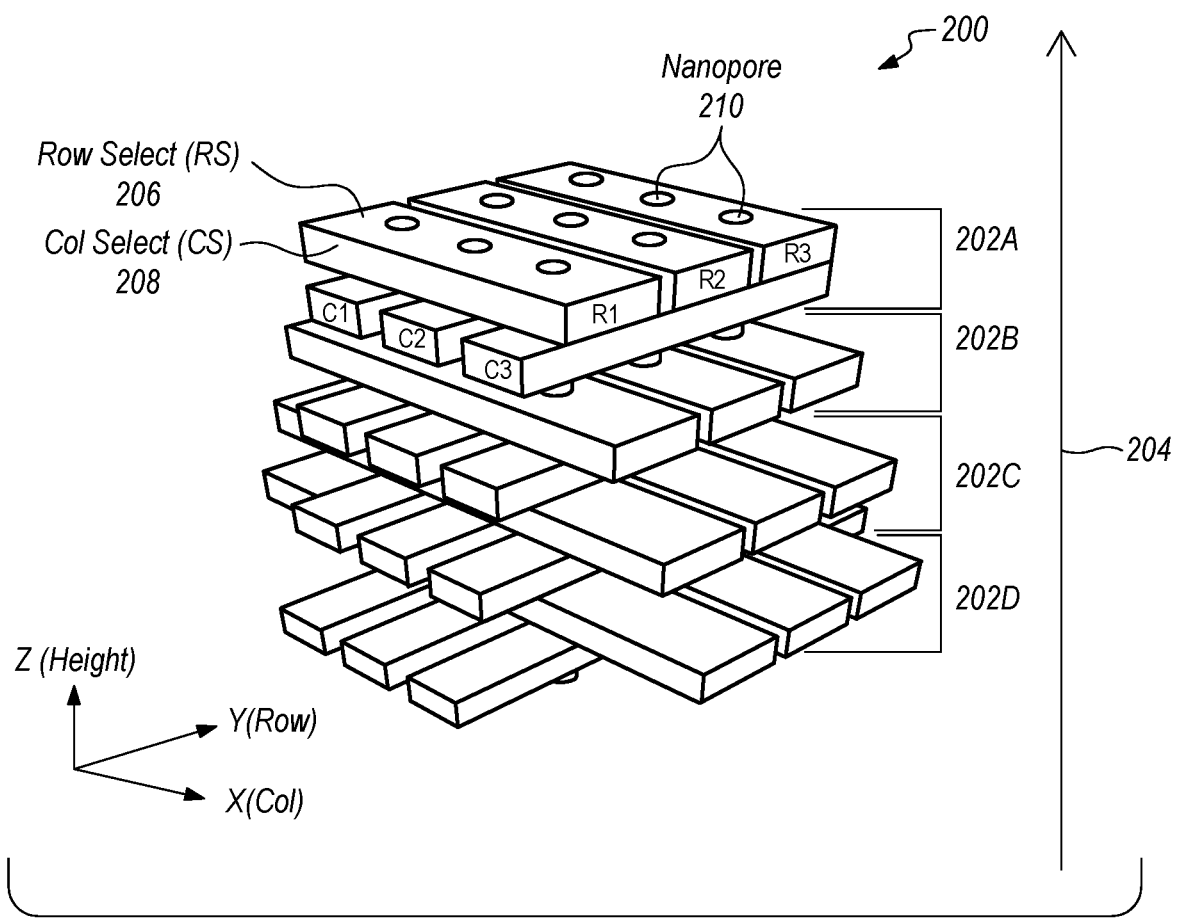
FIGS. 2A-2D schematically illustrate a 3D nanopore device according to one embodiment from perspective, top, front, and right views, respectively.
Figure 2B:
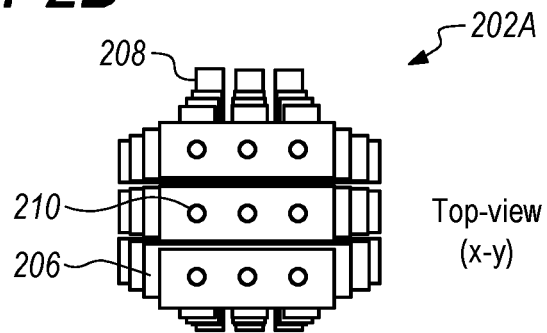
Figure 2C:
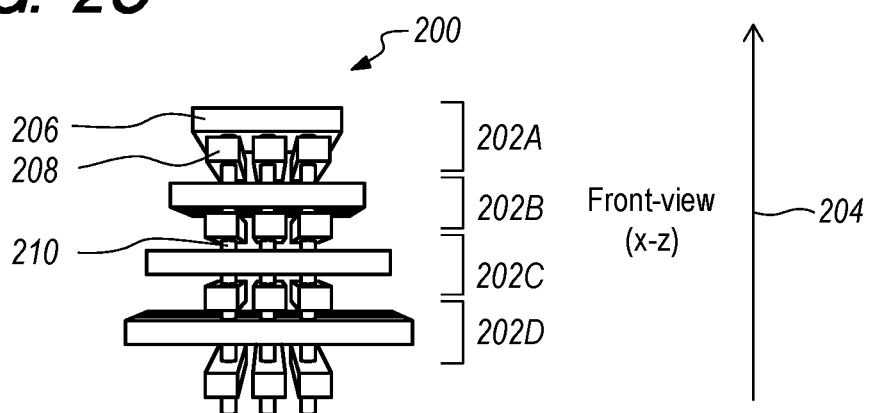
Figure 2D:
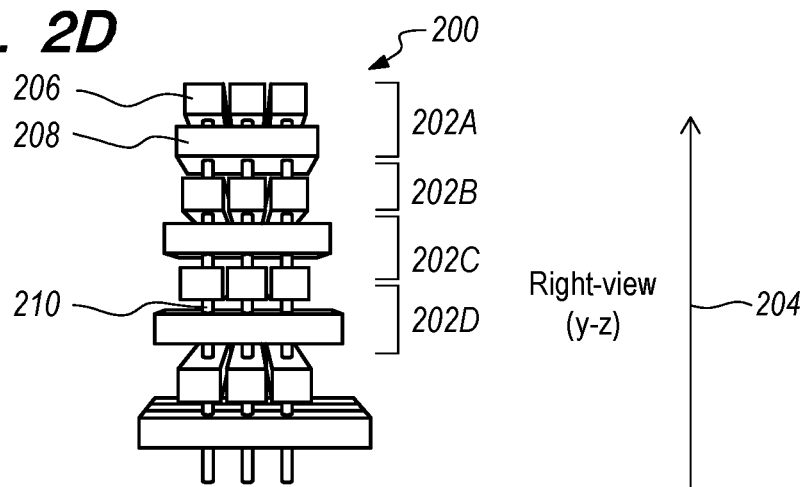

FIG. 2A-2D schematically depict various views of a nanopore device 200 incorporating solid-state nanopore technology with a three dimensional ("3D") array architecture according to one embodiment. As shown in FIG. 2A, the device 200 includes a plurality of 2D arrays or layers 202A-202D stacked along a Z axis 204. While the 2D arrays 202A-202D are referred to as "two dimensional," each of the 2D arrays 202A-202D has some thickness along the Z axis. FIG. 2B depicts a top view of the top 2D array 202A depicted in FIG. 2A. FIGS. 2C and 2D schematically depict front and right side views of the nanopore device 200 depicted in FIG. 2A.

The top 2D array 202A includes first and second selecting (inhibitory electrode) layers 206, 208 configured to direct movement of charged particles (e.g., biopolymers) through the nanopores 210 (pillars) formed in the first and second selecting layers 206, 208. The first selecting layer 206 is configured to select from a plurality of rows (R1-R3) in the 2D array 202A. The second selecting layer 208 is configured to select from a plurality of columns (C1-C3) in the 2D array 202A. In one embodiment, the first and second selecting layers 206, 208 select from the rows and columns, respectively, by modifying a charge adjacent the selected row and column and/or adjacent to the non-selected rows and columns. The other 2D arrays 202B-202D include rate control/current sensing electrodes. Rate control/sensing electrodes may be made of highly conductive metals, such as Ta, Al, Au—Cr, TiN, TaN, Pt, Cr, Graphene, Al—Cu, polysilicon, etc. The rate control/sensing electrodes may have a thickness of about 1~2 nm to about 1000 nm. Rate control/sensing electrodes may also be made in the biological layer in hybrid nanopores.

In the embodiment shown in FIGS. 2A-2D, each of the arrays 202A-202D is a two dimensional array having first and second layers 206, 208 arranged in a cross pattern. In other embodiments (not shown), at least some of the arrays 202A-202D (e.g., 202B-202D) may be one dimensional arrays having only a single layer of that is selectively addressable along one axis. Two such single layer arrays may be selectively addressable along respective axes that are orthogonal to each other. While the embodiment shown in FIGS. 2A-2D has four arrays 202A-202D, other embodiments (not shown) may have fewer or more layers.

Hybrid nanopores include a stable biological/biochemical component with solid-state components to form a semi-synthetic membrane porin to enhance stability of the nanopore. For instance, the biological component may be an αHL molecule. The αHL molecule may be inserted into a SiN based 3D nanopore. The αHL molecule may be induced to take on a structure to ensure alignment of the αHL molecule with the SiN based 3D nanopore by apply a bias to an electrode (e.g., in the top 2D array 202A).

The nanopore device 200 has a 3D vertical pillar stack array structure that provides a much larger surface area for charge detection than that of a conventional nanopore device having a planar structure. As a charged particle (e.g., biopolymer) passes through each 2D array 202A-202D in the device, its charge can be detected with a detector (e.g., electrode) in some of the 2D arrays 202B-202D. Therefore, the 3D array structure of the device 200 facilitates higher sensitivity, which can compensate for a low signal detector/electrode. Further, the highly integrated small form factor 3D structure provides a high density nanopore array while minimizing manufacturing cost.

In use, the nanopore device 200 is disposed between and separating top and bottom chambers (not shown) such that the top and bottom chambers are fluidly coupled by the nanopore pillars 210. The top and bottom chambers include an electrode (e.g., Ag/AgCl$_2$, etc.) and electrolyte solutions (De-ionized H$_2$O, KCl, LiCl$_2$) containing the charged particles (e.g., DNA) to be detected. Different electrode and electrolyte solutions can be used for the detection of different charged particles.

Electrophoretic charged particle translocation can be driven by applying a bias to electrodes disposed in a top chamber (not shown) adjacent the top 2D array 202A of the nanopore device 200 and a bottom chamber (not shown) adjacent the bottom 2D array 202D of the nanopore device 200. In some embodiments, the nanopore device 200 is disposed in a between top and bottom chambers (not shown) such that the top and bottom chambers are fluidly and electrically coupled by the nanopore pillars 210 in the nanopore device 200. The top and bottom chambers may contain the electrolyte solution.

Exemplary Nanopore Device Electrical Addressing Scheme

FIGS. 2A-2D depict, in perspective, top, and cross-sectional views, the nanopores 210 and the electrode (e.g., nanoelectrode) schemes according to one embodiment. In this embodiment, the nanopore 210 is surrounded by nanoelectrodes, allowing the nanopore 210 pillar channel to be controlled under nanoelectrode electrical bias field conditions.

The first and second selecting layers 206, 208 include cross-patterned nanogap electrodes that function as column and row inhibitory electrodes for the nanopore array device 200, respectively. Cross-patterned nanogap electrodes in the first and second selecting layers 206, 208 (see x-y plane view in FIG. 2B) are patterned using metal lithography techniques and the remaining electrodes in the other layers (202B-202D) are also deposited with cross-patterned or deposited with plane metal or poly gate electrodes. All the nanopore 210 pillar channels are completely surrounded by the metal or polysilicon electrodes and thus under the full influence of the electrical bias applied on the multiple stacked electrodes (in layers 202A-202D). By applying an inhibitory bias (e.g., 0V-VCC) to the nanogap electrodes in the first and second selecting layers 206, 208, a biomolecular translocation process through the nanopore array device 200 can be selectively inhibited, allowing the nanopore array device 200 to select and deselect particular rows and columns for operation. The inhibitory bias applied to the nanogap electrodes in the first and second selecting layers 206, 208 can generate an electrical field with sufficient strength to suppress ionic translocation of charged particles (e.g., biomolecules) through selected nanopore 210 pillar channels (e.g., from a top chamber to a bottom chamber orthogonal to the planes of the electrodes).

FIG. 3 schematically depicts a nanopore device 300 according to another embodiment. FIG. 3 depicts the top 2D array 302 in a cross-sectional (x-z plane) view showing the 3D nanopore 310 and nanoelectrode schemes. Each nanopore 310 is surrounded by nanoelectrodes 312, allowing the nanopore 310 channel to operate under an electric bias field condition generated using the nanoelectrodes 312. Cross-patterned nanogap nanoelectrodes 312CS-312Cn, 312RS-312Rn are disposed in two layers on top or the bottom two layers of the nanopore device 300. These nanoelectrodes 312CS-312Cn, 312RS-312Rn are column and row inhibitory nanoelectrodes 312CS-312Cn, 312RS-312Rn for the nanopore array, respectively. The cross-patterned nanoelectrodes 312CS-312Cn, 312RS-312Rn as shown in the top 2D array 302 (x-y plane view) may be formed/patterned at the metal or polysilicon lithography steps. Nanoelectrodes 312 in the remaining 2D arrays in the 3D stack may be formed by the cross patterned or plane depositing metal or polysilicon. The nanopore 310 hole pillars are surrounded by the metal or polysilicon nanoelectrodes 312CS-312Cn, 312RS-312Rn, and thus may operate under the full influence of the electrical bias applied to the multiple stacked nanoelectrodes 312.

By applying an inhibitory electrical bias (0V-VCC) to select nanogap nanoelectrodes 312CS-312Cn, 312RS-312Rn in the top 2D array 302, biomolecular translocation (e.g., electrophoretic) through one or more nanopores 302 in the top 2D nanopore array 302 can be inhibited to control nanopore array operation according to one embodiment. The electrical bias applied to the nanoelectrodes 312CS-312Cn, 312RS-312Rn can generate an electric field sufficient to suppress ionic translocation of charged particles (e.g., nucleic acids) from a top chamber (not shown) to a bottom chamber (not shown) in a direction orthogonal to the nanoelectrodes 312CS-312Cn, 312RS-312Rn. Nanoelectrode 312 mediated ionic translocation suppression can be substantially complete or the electrical bias can be modulated to only reduce the rate of ionic translocation. In one embodiment, after one or more nanopores 310 are selected (e.g., for DNA biomolecules translocation and sequencing), the electrical biases in a stack of 3D nanopore nanoelectrodes 312 can be modulated to control the biomolecular translocation speed. In one embodiment, the inhibitory electrical bias reduces/stops ionic current flow in the vertical direction to thereby select and/or deselect various columns and rows defined by the nanogap nanoelectrodes 312CS-312Cn, 312RS-312Rn. At the same time, the nanoelectrodes 312 can detect current modulations resulting from passage of charged particles (e.g., DNA biomolecules) through the 3D vertical nanopore 310 pillars. In some embodiments, the nanoelectrodes 312 can detect current modulations using a variety of principles, including ion blockade, tunneling, capacitive sensing, piezoelectric, and microwave-sensing.

Exemplary Nanopore Device Rate Control/Sensing Schemes

FIG. 4 is a table 400 illustrating the voltage operation of a nanopore device (e.g., the nanopore device 300 depicted in FIG. 3) according to various embodiments. As shown in FIG. 4, the nanopore device 300 can be operated in both inhibitory (of translocation), normal, and sensing modes by modulating the voltage/bias applied to various electrodes 312. VPP is from about 0V to about 2.5V; VCC is from about 0V to about 1.5V. All other electrodes are set to ground unless other specified in the table in FIG. 4. The height select electrode called Drain ("VZ"; see FIG. 3) is set to Vpp to apply the drain bias to the nanofluidic FET and opposite polarity for the drain is achieved by applying −Vpp on the electrode.

Due to conical shape of the Reactive Ion Etching (RIE) processed nanofluidic channel, biomolecular translocation through the pore opening of the bottom cross-patterned stacks can be more effective.

In inhibitory operation mode, the row and column voltages of the selected row ("SR") and the selected column ("SC") are both set to −VCC. The voltages of the unselected rows ("UR") and unselected columns ("UC") are set as VCC, selected rows (SR) and unselected columns (UC) and unselected rows (UR) and unselected columns (SC) are biased at (shown in the table in FIG. 4.

In sensing operation mode, the row and column voltages of the selected row ("SR") and the selected column ("SC") are set to sweep for Vth (threshold voltage) at particular IZ, respectively.

Exemplary Nanopore Device Rate Control Schemes

After a charged particle (e.g., a DNA biomolecule) enters a nanopore 310 pillar channel selected at a particular nanopore address in the array 302, a molecular flow takes place through the nanopore 310 pillar channel. This molecular flow is driven and directed by various electrical fields across the top and bottom chambers and through the stack of nanoelectrodes 312 allowing the control of the charged particle translocation speed as well as sensing of electrical characteristic changes related to the charged particle while is passes through the 3D vertical nanopore 310 pillar channel.

The translocation speed control mechanism is related to the surface charge of the walls of the nanopore 310 pillar channel. Nanoelectrode 312 gate modulation can induce enhancement of the charged particle (e.g., biomolecule) capture rate (by applying a positive gate voltage/bias across one or more rate control electrodes in the 3D array) thereby slowing translocation speed. On the other hand, applying a negative gate voltage/bias across one or more rate control electrodes in the 3D array can introduce an inhibitory force opposite to the biomolecular translocation direction, to thereby increase the translocation speed. Using these and other voltage/bias techniques, translocation speed can be maintained at levels that are optimal for sensing. Voltage/bias modulation to control translocation speed can be made more accurate by detecting translocation speed (e.g., via sensing, as described below) after each modulation pulse to refine control of the translocation speed.

Figure 5:
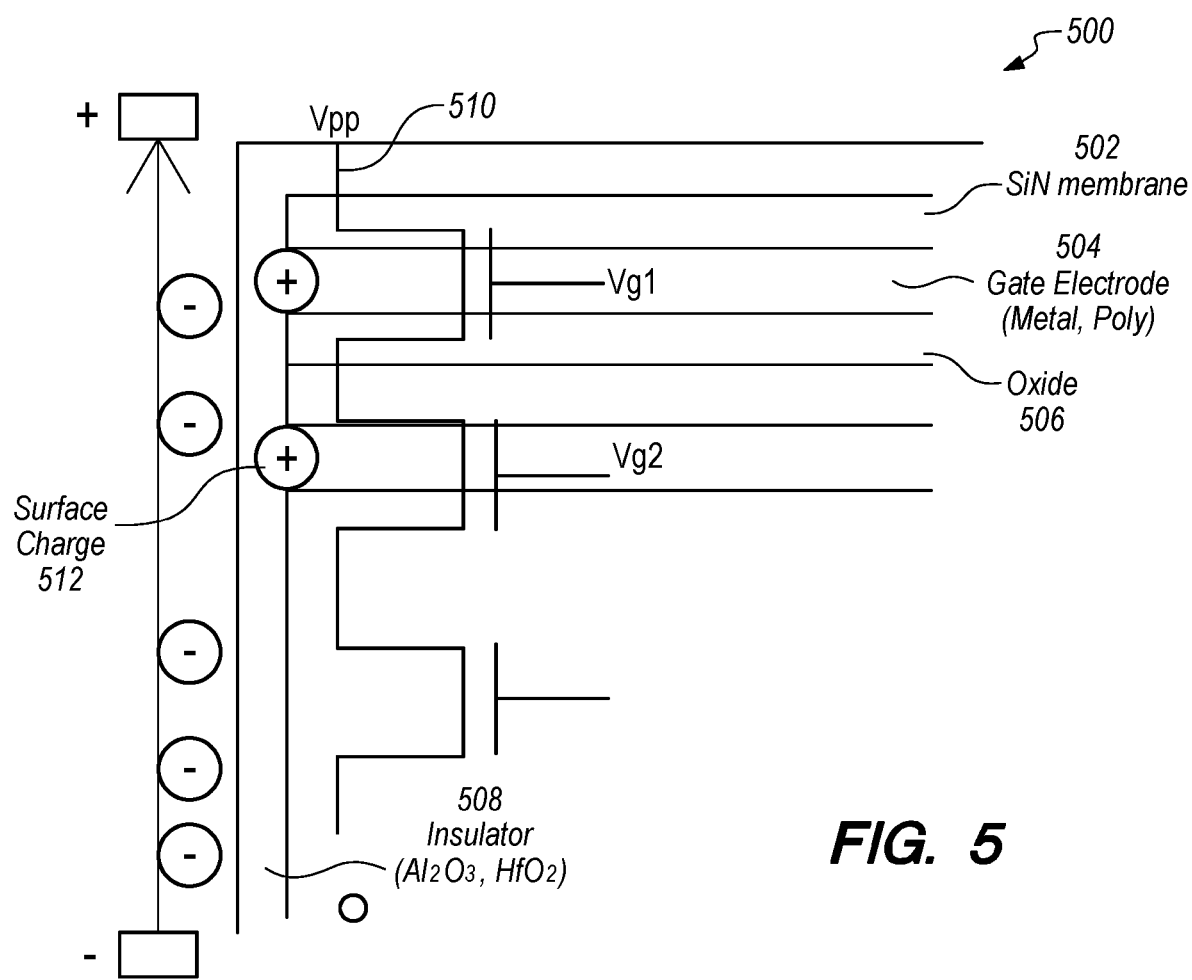
FIG. 5 schematically illustrates a portion of a 3D nanopore device according to one embodiment.

The bias scheme for the control rate for the nanoelectrode is summarized in the FIG. 4 (table described above) and FIG. 5. FIG. 5 schematically depicts a portion of a 3D nanopore sensor array 500 having a SiN membrane 502 on top of a transistor gate electrode (metal or polysilicon) 504 on top of an oxide 506. This series 502, 504, 506 is repeated to form a stack of rate control/sensing electrodes. The entire stack is covered with an insulator dielectric film 508 using thermal oxidation or ALD (atomic layer deposition) techniques (e.g., $SiO_2$, $Al_2O_3$, $HfO_2$, ZnO). The dielectric film's thickness is from about 2 nm to about 50 nm, and it can be used as a gate dielectric using $SiO_2$, $Al_2O_3$, $HfO_2$, or ZnO. The thickness of the transistor gate electrode 504 is the channel length (gate film thickness in this case) of the transistor and it can be made with polysilicon or metals. Exemplary methods of manufacturing multi-channel nanopore arrays such as those depicted in FIGS. 2A-2D, 3, and 5 are described in U.S. Provisional Patent Application Ser. Nos. 62/566,313 and 62/593,840 and U.S. Utility patent application Ser. No. 16/147,362, the contents of which have been previously incorporated by reference.

When a translocation rate control bias signal 510 for column and row voltages (e.g., Vpp, see "Normal Operation" in FIG. 4) is applied to the 3D nanopore sensor array 500, column and row Inhibitory voltage/bias pulses are followed by a verify (sensing) voltage/bias pulse (e.g., Vg1, Vg2), as described above. An exemplary signal 510 is depicted in FIG. 5 overlaid on top of the 3D nanopore sensor array 500. As described above with respect to "inhibitory operation" in FIG. 4, inhibitory biases are applied to deselect various column and row nanopore pillar channels, respectively. During sensing operation, both column and row inhibitory select electrodes are selected. The resulting surface charge 512 can be detected as a change in an electrical characteristic, such as current.

Figure 6:
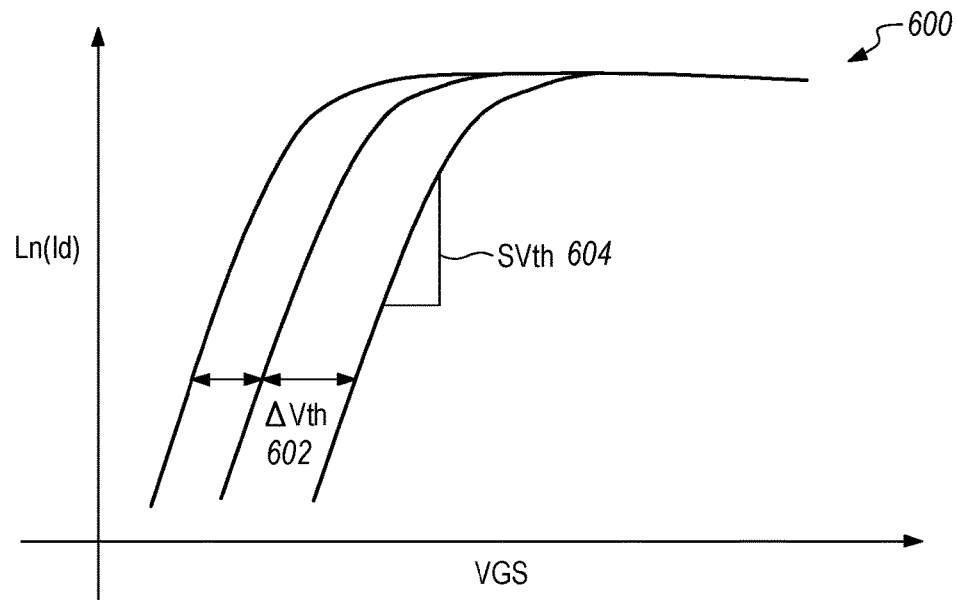
FIG. 6 is a plot depicting an inhibitory gate voltage/bias effect on a nanopore channel according to one embodiment.

FIG. 6 depicts an exemplary plot 600 showing an inhibitory gate voltage/bias effect on a nanopore channel. FIG. 6 plots the natural log of the drain current ("Ln(Id)") vs. gate to source voltage ("VGS"). When an inhibitory gate voltage/bias is applied, the field between the ionic channel and gate electrode is neutralized (change in threshold voltage "ΔVth" 602), resulting in a reduction of the ionic current flow, as shown in FIG. 6. In a linear portion of the graph, the graph has a slope "SVth" 604.

Figure 7:
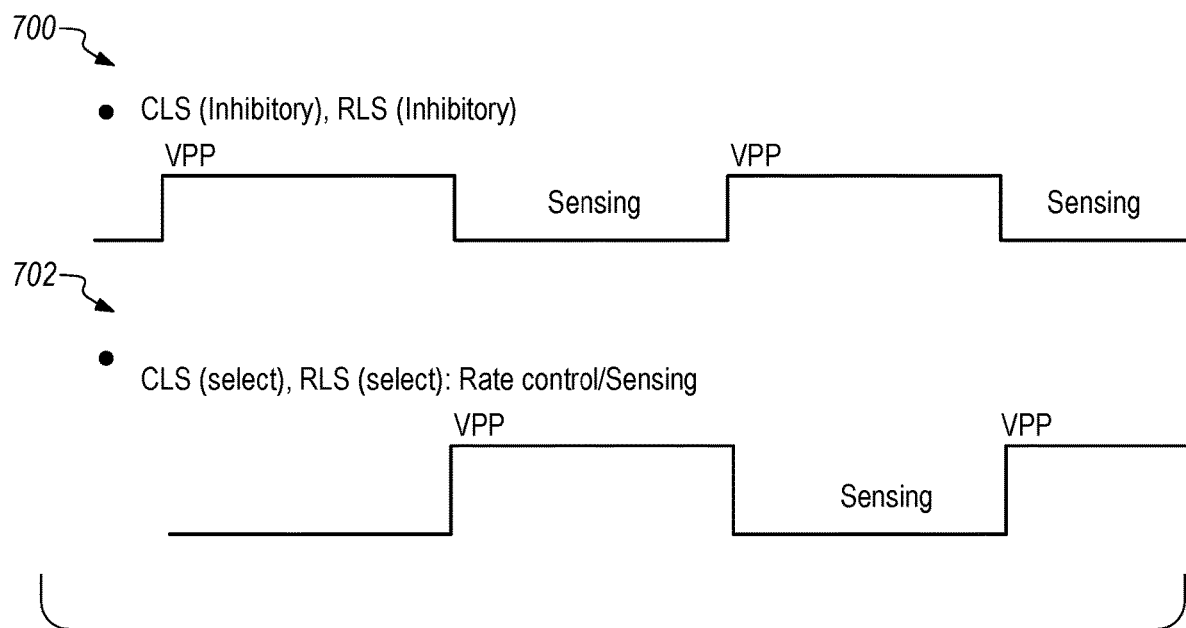
FIG. 7 is a plot illustrating electrode biasing schemes according to one embodiment.

FIG. 7 depicts electrode biasing schemes 700, 702 for electrode inhibition and selection/rate control/sensing according to one embodiment.

Figure 8A:
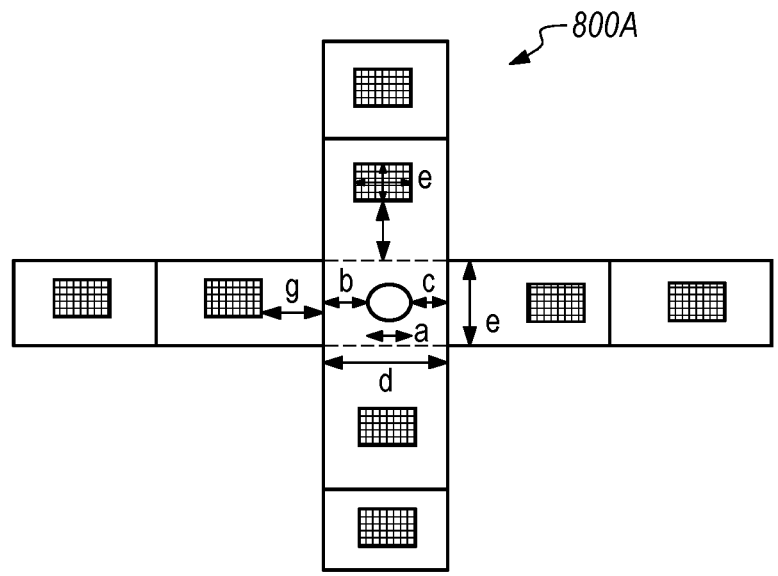
FIGS. 8A and 8B schematically illustrate electrode schemes according to two embodiments.
Figure 8B:
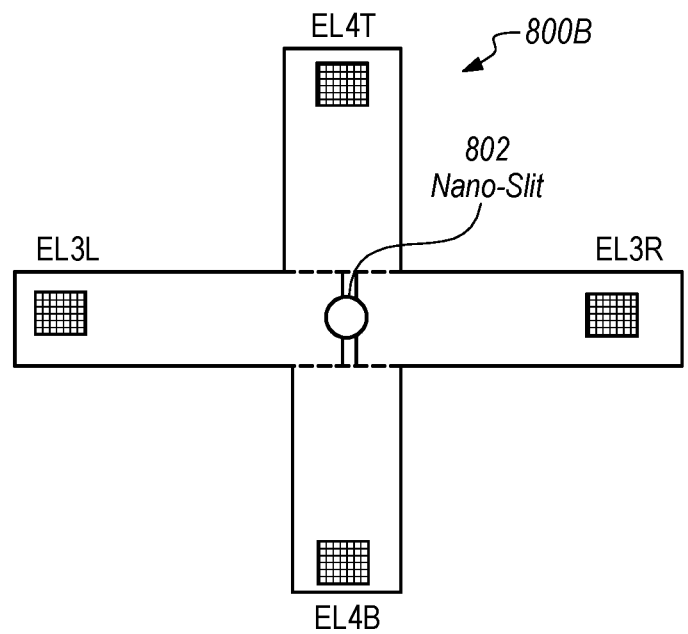

FIGS. 8A and 8B schematically depict electrode schemes according to two embodiments. The first electrode scheme 800A utilizes plates of metal for the row and column select electrodes (e.g., common electrode). The second electrode scheme 800B utilizes a cross-patterned metal electrode, which allows input and output electrodes to be co-located in a plane of metal by forming a nano-slit 802 in the center of the electrode plate.

Exemplary Nanopore Device Sensing Scheme/Nanofluidic FET Sensing

The surface charge density conditions of a nanopore pillar channel affect translocation performance in the nanopore pillar channel because biomolecules (e.g., DNA, RNA) are charged molecules in electrolyte solutions. As such, surface charge density can be modulated (e.g., location and magnitude) to increase or decrease translocation rates as described above. Nanopore sensing can use various electrical signal detection techniques for molecule detection and identification, including resistive pulse sensing and current-voltage ("I-V") detection.

Figure 9A:
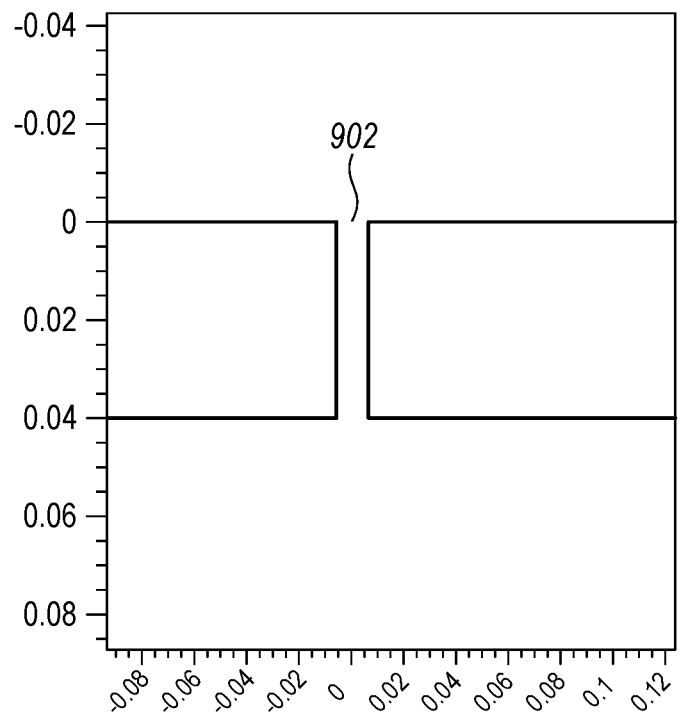
FIGS. 9A and 9B schematically illustrate a change in surface state charge of a nanofluidic field effect transistor according to one embodiment.
Figure 9B:
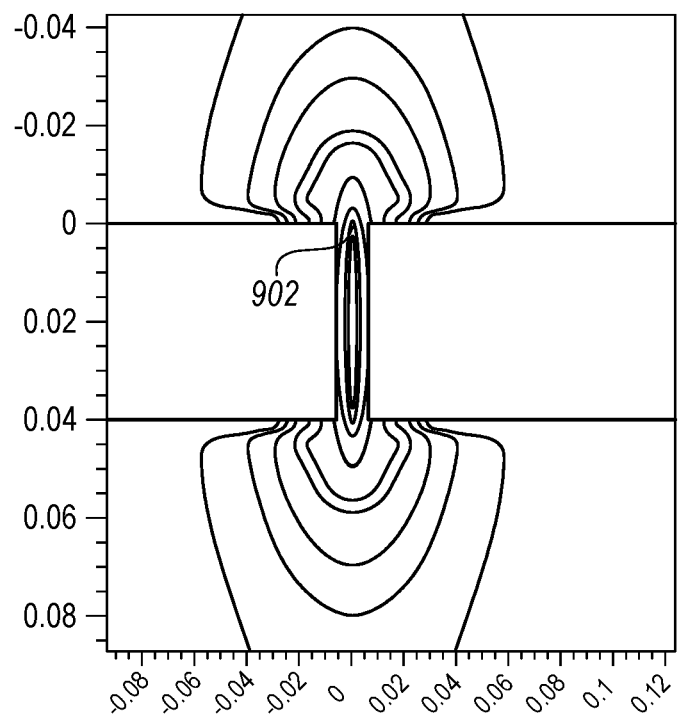

A sensing technique according to one embodiment uses a change in a surface state charge of a nanofluidic field effect transistor ("FET") inside a nanopore pillar channel stack as shown in FIGS. 9A and 9B. This FET sensing technique can be used in 3D or planar (2D) nanopore device architectures as long as embedded gate electrodes are used for the conductance modulation. The nanofluidic channel 902 inside the nanopore pillar is a conducting channel, the conductance of which can be modified by the varying the concentration of the electrolyte. If the electrolyte concentration in the nanofluidic channel 902 is adjusted optimally, the nanofluidic channel 902 can function in an analogous manner to a semiconductor channel.

The ionic current flows through the nanofluidic channel 902 will influence the surface charge of the nanopore pillar channel and thus the FET conductance showing the shift in the threshold voltage for each FET as shown in the FIGS. 9A and 9B. The control of the surface charge by the FET VGS (gate to source) and VDS (drain to source) can modulate the ionic transport flow and thus the translocation rate of the electrolyte and charged biomolecules in the nanopore pillar channel. Either negatively charged or positively charged biomolecules introduced in the nanofluidic channel 902 will influence the surface charge state of the FET, the polarity and amount of the charges can be monitored by the gate voltages represented by the changes in the threshold voltage and sub-threshold slope of the gate voltage of each transistor as illustrated in the FIG. 6. By monitoring the difference in the sub-threshold slope ("SVth") ΔVGS/Δ Ln(Id) of the nanofluidic channel, transconductance characteristics, ionic charge or biomolecular charge state can be accurately monitored.

Figure 10:
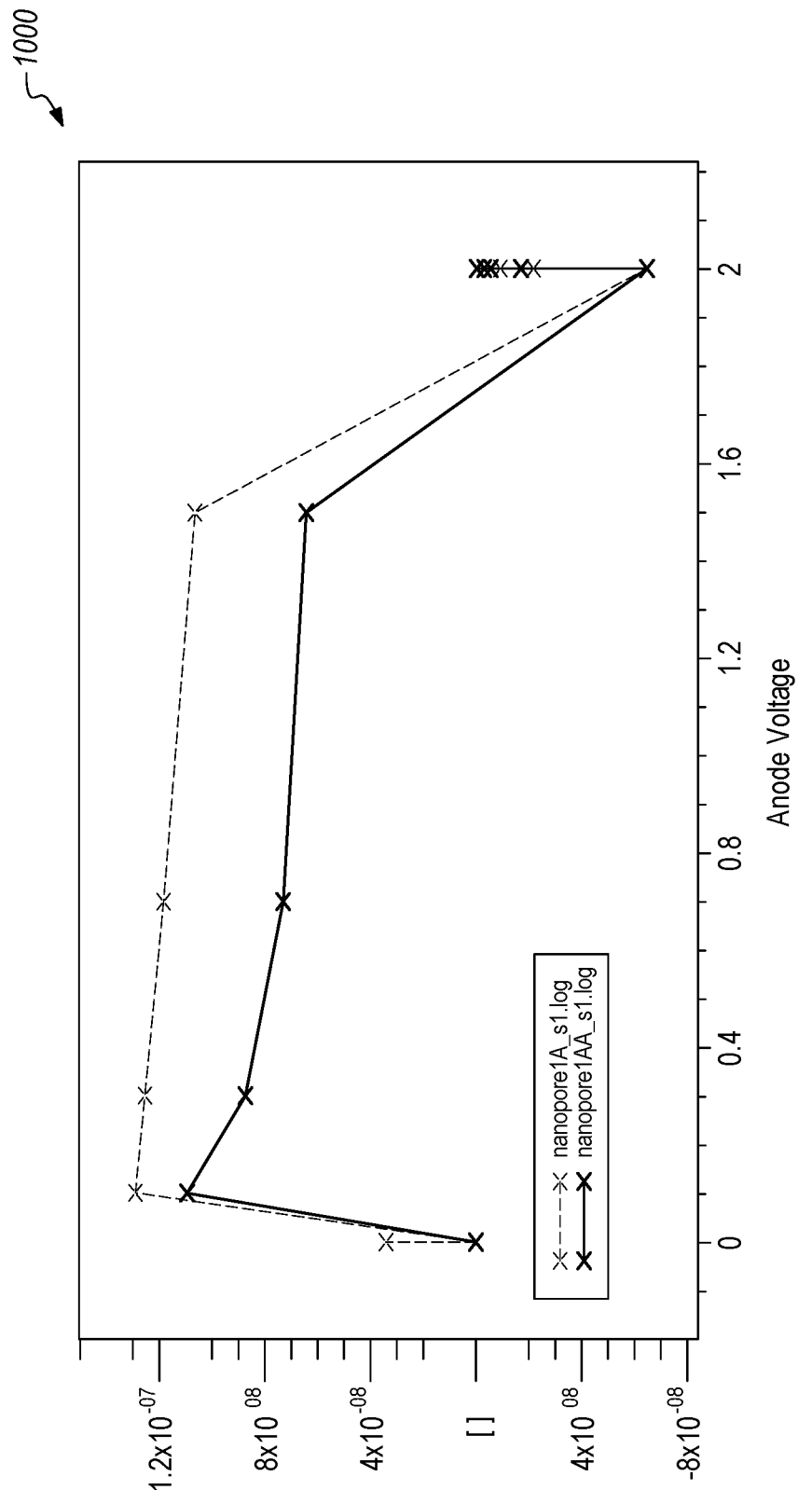
FIG. 10 is a plot of current vs anode voltage according to one embodiment.

FIG. 10 is a plot 1000 of current vs anode voltage according to one embodiment.

3D nanopore devices (e.g., 200, 300) allow either direct or targeted sequencing in an array while minimizing form-factor overhead, because the 2D arrays 202, 302 in the nanopore devices 200, 300 can be stacked vertically instead of positioned horizontally, thereby allowing for high density applications. Further, 3D nanopore devices (e.g., 200, 300) are scalable, with medium to large 3D nanopore devices having more than 1,000,000 nanopore 210, 310 pillars. Consequently, a larger number of sequencing sensors can be accommodated within the same form-factor. This parallel processing allows more sequencing sensors to be accommodated within a particular form factor.

The corresponding structures, materials, acts and equivalents of all means or step plus function elements in the claims below are intended to include any structures, materials, acts and equivalents for performing the function in combination with other claimed elements as specifically claimed. It is to be understood that while the invention has been described in conjunction with the above embodiments, the foregoing description and claims are not to limit the scope of the invention. Other aspects, advantages and modifications within the scope to the invention will be apparent to those skilled in the art to which the invention pertains.

Various exemplary embodiments of the invention are described herein. Reference is made to these examples in a non-limiting sense. They are provided to illustrate more broadly applicable aspects of the invention. Various changes may be made to the invention described and equivalents may be substituted without departing from the true spirit and scope of the invention. In addition, many modifications may be made to adapt a particular situation, material, composition of matter, process, process act(s) or step(s) to the objective(s), spirit or scope of the present invention. Further, as will be appreciated by those with skill in the art that each of the individual variations described and illustrated herein has discrete components and features which may be readily separated from or combined with the features of any of the other several embodiments without departing from the scope or spirit of the present inventions. All such modifications are intended to be within the scope of claims associated with this disclosure.

Any of the devices described for carrying out the subject diagnostic or interventional procedures may be provided in packaged combination for use in executing such interventions. These supply "kits" may further include instructions for use and be packaged in sterile trays or containers as commonly employed for such purposes.

The invention includes methods that may be performed using the subject devices. The methods may comprise the act of providing such a suitable device. Such provision may be performed by the end user. In other words, the "providing" act merely requires the end user obtain, access, approach, position, set-up, activate, power-up or otherwise act to provide the requisite device in the subject method. Methods recited herein may be carried out in any order of the recited events which is logically possible, as well as in the recited order of events.

Exemplary aspects of the invention, together with details regarding material selection and manufacture have been set forth above. Other details of the present invention, these may be appreciated in connection with the above-referenced patents and publications as well as generally known or appreciated by those with skill in the art. The same may hold true with respect to method-based aspects of the invention in terms of additional acts as commonly or logically employed.

In addition, though the invention has been described in reference to several examples optionally incorporating various features, the invention is not to be limited to that which is described or indicated as contemplated with respect to each variation of the invention. Various changes may be made to the invention described and equivalents (whether recited herein or not included for the sake of some brevity) may be substituted without departing from the true spirit and scope of the invention. In addition, where a range of values is provided, it is understood that every intervening value, between the upper and lower limit of that range and any other stated or intervening value in that stated range, is encompassed within the invention.

Also, it is contemplated that any optional feature of the inventive variations described may be set forth and claimed independently, or in combination with any one or more of the features described herein. Reference to a singular item, includes the possibility that there are plural of the same items present. More specifically, as used herein and in claims associated hereto, the singular forms "a," "an," "said," and "the" include plural referents unless the specifically stated otherwise. In other words, use of the articles allow for "at least one" of the subject item in the description above as well as claims associated with this disclosure. It is further noted that such claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in claims associated with this disclosure shall allow for the inclusion of any additional element—irrespective of whether a given number of elements are enumerated in such claims, or the addition of a feature could be regarded as transforming the nature of an element set forth in such claims. Except as specifically defined herein, all technical and scientific terms used herein are to be given as broad a commonly understood meaning as possible while maintaining claim validity.

The breadth of the present invention is not to be limited to the examples provided and/or the subject specification, but rather only by the scope of claim language associated with this disclosure.

What is claimed is:

1. A nanopore device for characterizing biopolymer molecules, comprising:
   a first selecting layer having a first plurality of independently addressable inhibitory electrodes disposed along a first axis of selection; and
   a second selecting layer having a second plurality of independently addressable inhibitory electrodes disposed along a second axis of selection orthogonal to the first axis of selection, wherein the second selecting layer is disposed adjacent the first selecting layer, such that the first selecting layer, and the second selecting layer form a stack of layers along a Z axis and define a plurality of nanopore pillars.

2. The device of claim 1, wherein the plurality of nanopore pillars is disposed in an array of nanopore pillars along a plane orthogonal to the Z axis.

3. The device of claim 2, wherein each of the first plurality of inhibitory electrodes is independently addressable to select a respective row of nanopore pillars from the array of nanopore pillars.

4. The device of claim 2, wherein each of the second plurality of inhibitory electrodes is independently addressable to select a respective column of nanopore pillars from the array of nanopore pillars.

5. The device of claim 2, wherein one of the first plurality of inhibitory electrodes and one of the second plurality of inhibitory electrodes are independently addressable to select a nanopore pillar from the array of nanopore pillars.

6. The device of claim 2, wherein the first and second pluralities of inhibitory electrodes are cross-patterned electrodes.

7. The device of claim 2, wherein each pair of the first plurality of inhibitory electrodes is independently addressable to select a respective row of nanopore pillars from the array of nanopore pillars.

8. The device of claim 2, wherein each pair of the second plurality of inhibitory electrodes is independently addressable to select a respective column of nanopore pillars from the array of nanopore pillars.

9. The device of claim 2, wherein respective pairs of the first and second pluralities of inhibitory electrodes are independently addressable to select a nanopore pillar from the array of nanopore pillars.

10. The device of claim 2, wherein the first and second pluralities of inhibitory electrodes are configured to select a nanopore pillar from the array of nanopore pillars by applying a first inhibitory bias to all of the first plurality of inhibitory electrodes except a first inhibitory electrode corresponding to a selected row and applying a second inhibitory bias to all of the second plurality of inhibitory electrodes except a second inhibitory electrode corresponding to a selected column.

11. The device of claim 10, wherein the first and second inhibitory biases generate respective first and second electric fields sufficient to suppress ionic translocation.

12. The device of claim 1, wherein the first and second pluralities of inhibitory electrodes are respective nanoelectrodes.

13. The device of claim 1, wherein the nanopore device forms part of a solid-state, biological, or hybrid system.

14. The device of claim 1, wherein the nanopore device forms part of a 3D system.

15. The device of claim 1, wherein the nanopore device forms part of a 2D system.

16. The device of claim 1, wherein the first and second pluralities of inhibitory electrodes are formed using a lithography technique.

17. A nanopore device for characterizing biopolymer molecules, comprising a plurality of arrays disposed along a longitudinal axis, each array having:
a first selecting layer having a first plurality of independently addressable electrodes disposed along a first axis of selection; and
a second selecting layer having a second plurality of independently addressable electrodes disposed along a second axis of selection orthogonal to the first axis of selection,
wherein the first and second pluralities of independently addressable electrodes defines a plurality of nanopore pillars.

18. The device of claim 17, wherein a top array of the plurality comprises first and second inhibitory electrodes.

19. The device of claim 18, wherein the other arrays of the plurality comprise translocation rate control and sensing electrodes.

20. The device of claim 17, wherein a bottom array of the plurality comprises first and second inhibitory electrodes.

* * * * *